(12) United States Patent
Chu et al.

(10) Patent No.: US 7,385,682 B2
(45) Date of Patent: Jun. 10, 2008

(54) CYTOMETER

(75) Inventors: Jianjun Chu, Shenzhen (CN); Yingchun Li, Shenzhen (CN)

(73) Assignee: Shenzhen Mindray Bio-Medical Electronics Co., Ltd. (CN)

( * ) Notice: Subject to any disclaimer, the term of this patent is extended or adjusted under 35 U.S.C. 154(b) by 0 days.

(21) Appl. No.: 11/516,657

(22) Filed: Sep. 7, 2006

(65) Prior Publication Data
US 2007/0159619 A1    Jul. 12, 2007

(30) Foreign Application Priority Data
Jan. 9, 2006    (CN) ............... 2006 1 0020150

(51) Int. Cl.
G01N 21/00    (2006.01)
(52) U.S. Cl. .................................... 356/73
(58) Field of Classification Search ............... None
See application file for complete search history.

(56) References Cited

U.S. PATENT DOCUMENTS

| | | | |
|---|---|---|---|
| 5,426,499 A | 6/1995 | Kosaka et al. | |
| 5,788,927 A | 8/1998 | Farrell et al. | |
| 5,831,723 A | 11/1998 | Kubota et al. | |
| 5,872,627 A * | 2/1999 | Miers | 356/338 |
| 6,713,019 B2 | 3/2004 | Ozasa et al. | |
| 7,113,266 B1 * | 9/2006 | Wells | 356/73 |

FOREIGN PATENT DOCUMENTS

CN    1116708 A    2/1996

* cited by examiner

Primary Examiner—Tu T Nguyen
(74) Attorney, Agent, or Firm—Bingham McCutchen LLP

(57) ABSTRACT

A cytometer includes an illuminating unit having a laser and a light beam shaping module for shaping and converging the laser beam emitted from the laser. A sample generation unit includes a gas-liquid transmission controlling module and a flow chamber which are connected to each other, so the sample liquid containing the cells to be detected may flow through the flow chamber while being encircled by the sheath fluid. A signal processing unit receives, converts and processes the scattering light emitted from the flow chamber. The signal processing unit includes at least a photoelectric detection module, wherein the light beam shaping module has at least one aspheric collimating lens and a pair of mutually crossing cylindrical lenses, and the numerical aperture of the aspheric collimating lens is at least 0.3.

13 Claims, 10 Drawing Sheets

A) Beam spot

B) Distribution

CYTOMETER

STATEMENT OF RELATED APPLICATION

This application claims the benefit of priority to China Patent Appl. No.: 200610020150.4, filed Jan. 9, 2006, entitled "Cytometer".

FIELD OF THE INVENTION

The present invention relates to a flow cytometer, in particular, to a blood cell cytometer.

BACKGROUND OF THE INVENTION

Conventional flow cytometers have been widely used in the analysis of blood cells. Such a blood cell cytometer is mainly comprised of an illuminating unit, a flow chamber and a signal processing unit. The flow chamber provides an optical cell-interrogation zone, in which a flow of the sample of blood cells is encircled in a sheath flow according to the fluid focusing principle, so that the blood cells pass through the detection passage one by one; the illuminating unit, usually a laser, provides an illuminating light beam which may irradiate into the cell-interrogation zone of the flow chamber, such that the illuminating light beam may irradiate onto the cells flowing through the cell-interrogation zone so as to be scattered, or excite fluorescence emission, etc.; and the signal processing unit is useful for collecting various optical information generated in the flow chamber and converting it into electric signals. By processing and analyzing these converted electric signals, the parameters of various cells contained in the blood can be obtained in order for subsequent processing such as counting and classification, etc.

Normally, certain properties of cells are all represented by the peak or pulse width of the signals described above, thus it is necessary to obtain such data as the peak or pulse width of various optical information, and some parameters concerning the blood cells may be calculated by using a histogram or scatter diagram plotted with these data.

In prior art, as shown in FIG. 1, a typical flow cytometer has to pass the light beam LB eradiated from a light source through the optical system which focuses the beam on the center of the cell-interrogation zone of the flow chamber 4, forming an elliptical spot BS on a plane $\pi$ perpendicular to the optical axis at the center of the cell-interrogation zone, and the minor axis of the spot should coincide with the flowing direction $\hat{f}$ of the sample. Since the light beam has a very large divergence angle $\theta_y$ in the direction of the cell flow, a significant aberration in particular a spherical aberration occurs after the light beam passes through the optical system, such that the spot focused at the cell-interrogation zone of the flow chamber, besides a main spot BS0 in the sample flowing direction, also has two symmetrical sidelobes BS1 and BS2, as shown in FIG. 2, in which I denotes the inner wall of the flow chamber and O the outer wall of the flow chamber. Thereby, the signal generated by the cells passing through such an illuminated region will correspondingly comprise sidelobs $P^{(1)}$ and $P^{(2)}$ at both sides of the main pulse signal P. If the amplitudes of these pulses are also to be identified as the scattered signals of cells, the result of the sample detection would be incorrect.

In a prior art approach for resolving this problem, a scattered pulse signal recognition algorithm is incorporated in the signal processing unit, getting rid of the sidelobs via a threshold value $V_{th}$. As shown in FIG. 3, when a peak as recognized is smaller than this threshold value, it is deemed to be a false signal and is rejected. However, this approach has a significant disadvantage in that usually the main pulse $P_k$ of some smaller cells is even smaller than the associated pulse of the bigger cells, and the real scattered signal $P_k$ of the small cells would be rejected along with the associated pulse of the bigger cells by using the threshold value, which will bring error to the cell analysis.

As disclosed in U.S. Pat. No. 6,713,019, a negative cylindrical lens (concave cylindrical lens) is used for eliminating the aberration in y direction so as to avoid the disturbance of the associated pulse. However, this approach has the following drawbacks: the complexity of the optical system, the dimension of the structure, and the difficulties upon assembly and adjustment are all increased; while minimizing the error in y direction, the concave cylindrical lens also influences the x direction, as a result of which the flat top effect upon light beam shaping is poor, which further affects the overall performance of the system; for certain systems requiring irradiation with multi-wavelength, the compensation effect of such a concave cylindrical lens is inconsistent, and it is still needed to increase the complexity of the signal recognition algorithm.

As disclosed in U.S. Pat. No. 5,788,927, an aspheric lens is used for collimating the light beam from the semiconductor laser, which is then focused via a space filter and a spherical lens to create an elliptical spot that irradiates into the flow cell. Although this approach also functions to eliminate the sidelobs, the application of the space filter enlarges the size of the structure and increases the difficulty upon assembly and adjustment. Furthermore, one spherical lens is incapable of forming a flat top in x direction, leading to aberration if the cells are introduced into the irradiated region from different positions.

SUMMARY OF THE INVENTION

The object of the present invention is to provide a cytometer, which eliminates the sidelobs of the scattered signal while achieving light beam shaping using a simple structure, so as to avoid the inaccuracy upon signal processing and overcome the deficiency in prior art.

According to the first aspect of the present invention, there is provided a cytometer comprising: an illuminating unit, which comprises a laser and a light beam shaping module for shaping and converging the laser light beam emitted from the laser so that the light beam irradiates samples to be detected; a sample generation unit, which comprises a gas-liquid transmission controlling module and a flow chamber that are connected to each other, so that the sample liquid containing the cells to be detected may flow through the flow chamber while being encircled by the sheath fluid; and a signal processing unit, which comprises at least a photoelectric detection module and is used for receiving, photoelectrically converting and correspondingly processing the scattering light emitted from the flow chamber; wherein the light beam shaping module comprises at least one aspheric collimating lens with a large numerical aperture and a pair of mutually crossing cylindrical lenses.

Preferably, the numerical aperture of the aspheric collimating lens is at least 0.3. The collimating lens comprises a first lens surface and a second lens surface, wherein the first lens surface is the incidence plane of the laser light beam. The lens surfaces of the aspheric collimating lens satisfy the following formula:

$$z = \frac{cr^2}{1+\sqrt{1-(1+k)c^2r^2}} + \alpha_1 r^2 + \alpha_2 r^4,$$

in which c is the curvature, z is the axial distance of the cross-section from a fixed point, k is a quadratic constant, and r is the radius of the cross-section; and the parameters of the first lens surface and second lens surface are as follows:

|  | c | k | α1 | α2 |
|---|---|---|---|---|
| First lens surface | 0.068609 | −87.228063 | 9.15754E−04 | −8.64353E−05 |
| Second lens surface | −0.23148106 | −0.648067 | −1.65853E−04 | 8.28138E−06 |

The light beam shaping module outputs a light beam with an elliptical cross section, which irradiates into the flow chamber. Preferably, the length of the minor axis of the ellipse is about 15 μm-25 μm, and that of the major axis is about 160 μm-220 μm, wherein the direction of the minor axis coincides with the flowing direction of the liquid within the flow chamber, and the direction of the major axis is perpendicular to the plane which is defined by the flowing direction of the liquid and the transmitting direction of the light beam. The irradiation depth of the light beam is about 8 μm-12 μm, and the light intensity is uniformly distributed at a segment in the direction of the major axis.

The signal processing unit comprises a photoelectric detection module, a signal extraction module and an analysis module which are connected in series; wherein the photoelectric detection module is used for collecting the scattering light in different angle ranges onto the photoelectric converter, so that the optical information out of the scattering light is converted into corresponding electrical signal which is then sent to the signal extraction module; the signal extraction module is used for extracting the peak or pulse width information from the signal so that such information is sent to the analysis module; and the analysis module is used for counting and classifying the received signals to form a one-dimensional histogram or two-dimensional scatter diagram. The photoelectric detection module comprises two sets of photoelectric signal collecting sub-modules for respectively collecting optical signals with different scattering angles, and corresponding photoelectric converters for performing corresponding photoelectric conversion for the optical signals.

According to the second aspect of the present invention, there is provided another cytometer comprising: an illuminating unit, which comprises a laser and a light beam shaping module for shaping and converging the laser light beam emitted from the laser so that the light beam irradiates the samples to be detected; a sample generation unit, which comprises a gas-liquid transmission controlling module and a flow chamber that are connected to each other, so that the sample liquid containing the cells to be detected may flow through the flow chamber while being encircled by the sheath fluid; and a signal processing unit, which comprises at least a photoelectric detection module and is used for receiving, photoelectrically converting and- correspondingly processing the scattering light emitted from the flow chamber; wherein the light beam shaping module comprises at least one aspheric collimating lens with the numerical aperture no less than 0.3.

Optionally, the light beam shaping module may further comprise a pair of mutually crossing cylindrical lenses.

The collimating lens comprises a first lens surface and a second lens surface, wherein the first lens surface is the incidence plane of the laser light beam. Preferably, the lens surfaces of the aspheric collimating lens satisfy the following formula:

$$z = \frac{cr^2}{1+\sqrt{1-(1+k)c^2r^2}} + \alpha_1 r^2 + \alpha_2 r^4,$$

in which c is the curvature, z is the axial distance of the cross-section from the fixed point, k is a quadratic constant, and r is the radius of the cross-section; and the parameters of the first lens surface and second lens surface are as follows:

|  | c | k | α1 | α2 |
|---|---|---|---|---|
| First lens surface | 0.068609 | −87.228063 | 9.15754E−04 | −8.64353E−05 |
| Second lens surface | −0.23148106 | −0.648067 | −1.65853E−04 | 8.28138E−06 |

The light beam shaping module outputs a light beam with an elliptical cross section, which irradiates into the flow chamber. Preferably, the length of the minor axis of the ellipse is about 15 μm-25 μm, and that of the major axis is about 160 μm-220 μm, wherein the direction of the minor axis coincides with the flowing direction of the liquid within the flow chamber, and the direction of the major axis is perpendicular to the plane which is defined by the flowing direction of the liquid and the transmitting direction of the light beam, and the irradiation depth of the light beam is about 8 μm-12 μm.

The signal processing unit comprises a photoelectric detection module, a signal extraction module and an analysis module which are connected in series; wherein the photoelectric detection module is used for collecting the scattering light in different angle ranges onto the photoelectric converter, so that the optical information out of the scattering light is converted into the corresponding electrical signal which is then sent to the signal extraction module; the signal extraction module is used for extracting the peak or pulse width information from the signal so that such information is sent to the analysis module; and the analysis module is used for counting and classifying the received signals to form a one-dimensional histogram or two-dimensional scatter diagram. The photoelectric detection module comprises two sets of photoelectric signal collecting sub-modules for respectively collecting optical signals with different scattering angles, and corresponding photoelectric converters for performing corresponding photoelectric conversion for the optical signals.

According to the third aspect of the present invention, there is provided still another cytometer comprising :an illuminating unit, which comprises a laser and a light beam shaping module for shaping and converging the laser light beam emitted from the laser so that the light beam irradiates the samples to be detected; a sample generation unit, which comprises a gas-liquid transmission controlling module and a flow chamber that are connected to each other, so that the sample liquid containing the cells to be detected may flow through the flow chamber while being encircled by the sheath fluid; and a signal processing unit, which comprises at least a photoelectric detection module and is used for receiving, photoelectrically converting and correspondingly processing the scattering light emitted from the flow chamber; wherein the photoelectric detection module comprises at least one aspheric collimating lens for collimating the scattering light beam emitted from the flow chamber.

Optionally, the light beam shaping module may further comprise a pair of mutually crossing cylindrical lenses.

Preferably, the numerical aperture of the aspheric collimating lens is at least 0.4. The collimating lens comprises a first lens surface and a second lens surface, wherein the first lens surface is the incidence plane of the laser light beam. The lens surfaces of the collimating lens satisfy the following formula:

$$z = \frac{cr^2}{1+\sqrt{1-(1+k)c^2r^2}} + \alpha_1 r^2 + \alpha_2 r^4 + \alpha_3 r^6,$$

in which c is the curvature, z is the axial distance of the cross-section from the fixed point, k is a quadratic constant, and r is the radius of the cross-section.

The light beam shaping module outputs a light beam with an elliptical cross section, which irradiates into the flow chamber. Preferably, the length of the minor axis of the ellipse is about 15 µm-25 µm, and that-of the major axis is about 160 µm-220 µm, wherein the direction of the minor axis coincides with the flowing direction of the liquid within the flow chamber, and the direction of the major axis is perpendicular to the plane which is defined by the flowing direction of the liquid and the transmitting direction of the light beam; and the irradiation depth of the light beam is about 8 µm-12 µm.

The signal processing unit comprises a photoelectric detection module, a signal extraction module and an analysis module which are connected in series; wherein the photoelectric detection module is used for collecting the scattering light in different angle ranges onto the photoelectric converter, so that the optical information out of the scattering light is converted into the corresponding electrical signal which is then sent to the signal extraction module; the signal extraction module is used for extracting the peak or pulse width information from the signal so that such information is sent to the analysis module; and the analysis module is used for counting and classifying the received signals to form a one-dimensional histogram or two-dimensional scatter diagram. The photoelectric detection module comprises two sets of photoelectric signal collecting sub-modules for respectively collecting optical signals with different scattering angles, and corresponding photoelectric converters for performing corresponding photoelectric conversion for the optical signals.

The laser is preferably a semiconductor laser.

The advantage of the present invention is as follows. In the present invention, while achieving light beam shaping with a pair of mutually crossing cylindrical lenses, an aspheric lens with a large numerical aperture (e.g., 0.3-0.5) is used for collimating the light beam with a large scattering angle. Thereby, the present invention eliminates the side lobes of the irradiating spot at the cell-interrogation zone of the flow chamber by way of the optical system and avoids the disturbance of the false pulse of the scattered signal to the light beam path, which renders the result of the detection more accurate. The realization of such accuracy is ensured by the design of the optical system and is an intrinsic feature, without signal processing needed for the related eliminating process, so that signal processing becomes simpler and more direct, providing the present invention with improved practicability.

The collimating lens of the present invention takes the form of an aspheric collimating lens, and the lens surface thereof satisfies the following formula:

$$z = \frac{cr^2}{1+\sqrt{1-(1+k)c^2r^2}} + \alpha_1 r^2 + \alpha_2 r^4 + \alpha_3 r^6 + \cdots.$$

Such an aspheric collimating lens guarantees the acquisition of a large numerical aperture, so that the elimination of the side lobes of the irradiating spot is ensured.

Additionally, the present invention uses a semiconductor laser, so that the structural dimension of the instrument system is significantly reduced.

DETAILED DESCRIPTION OF THE INVENTION

The invention is described in greater details below with reference to the accompanying drawings and the illustrative embodiments.

Referring to FIGS. 4-12, the cytometer according to the present invention comprises an illuminating unit 1, a sample generation unit 2 and a signal processing unit 3 which are connected in series.

Figure 1:
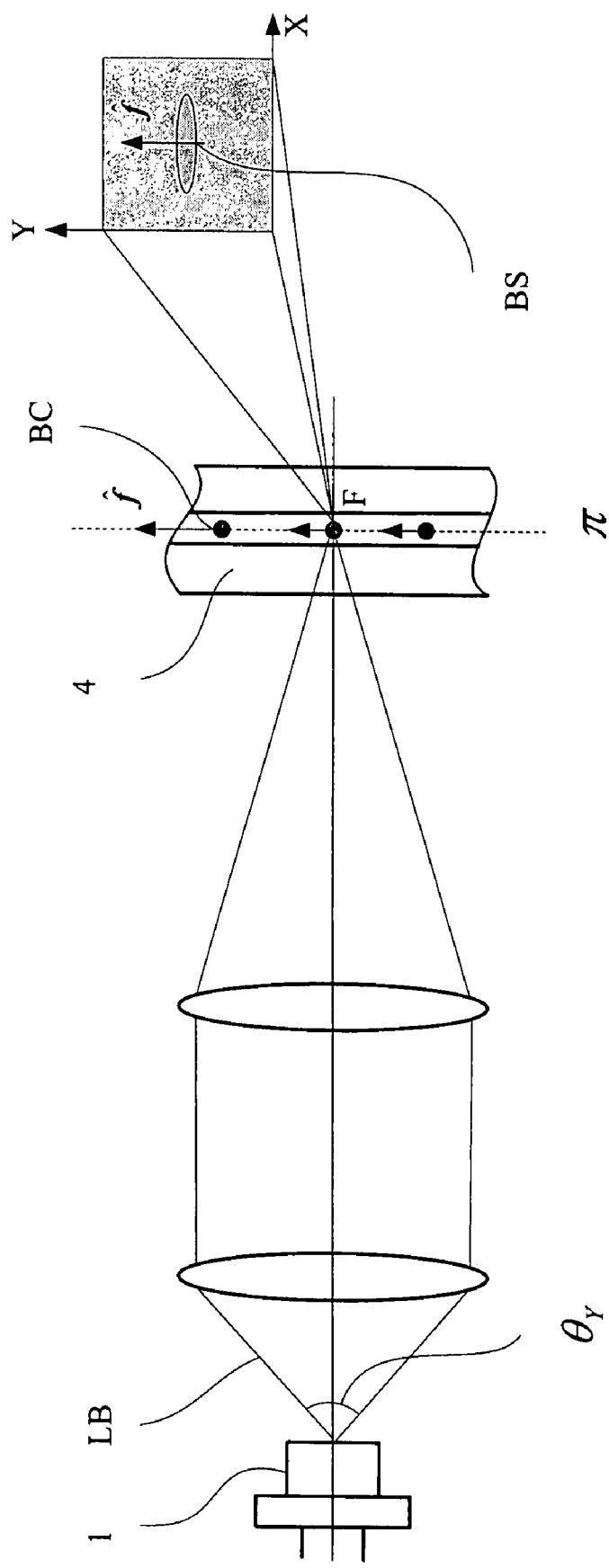
FIG. 1 is a schematic view of a flow cytometer in prior art.
Figure 2:
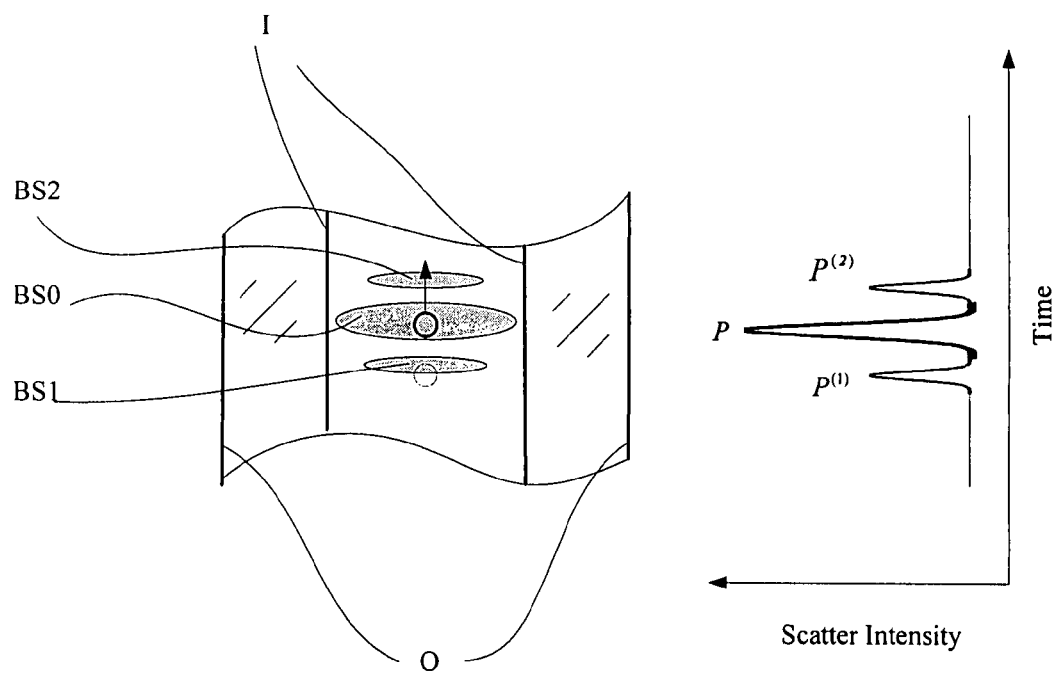
FIG. 2 is a schematic view illustrating the defect of a scattered signal in prior art.
Figure 3:
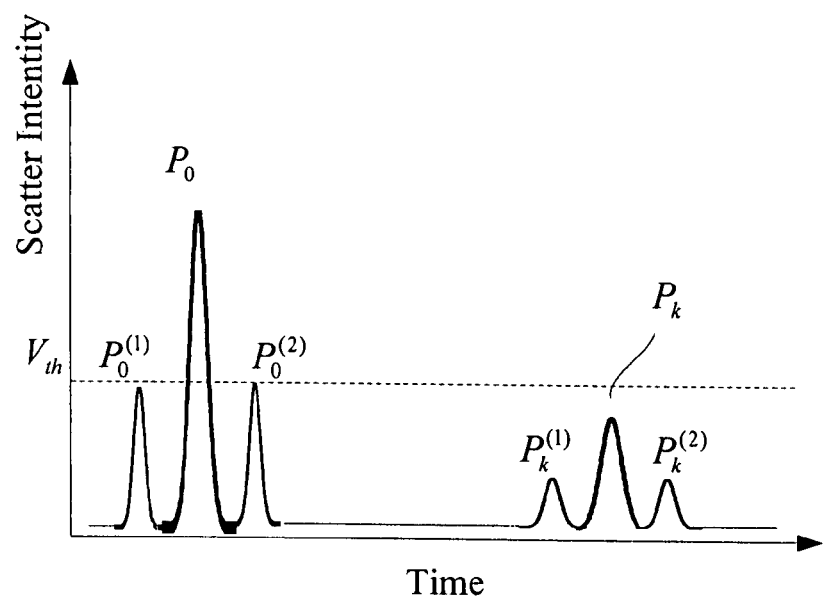
FIG. 3 is a schematic view illustrating the method of eliminating the defect of an associated pulse using a threshold value in prior art.
Figure 4:
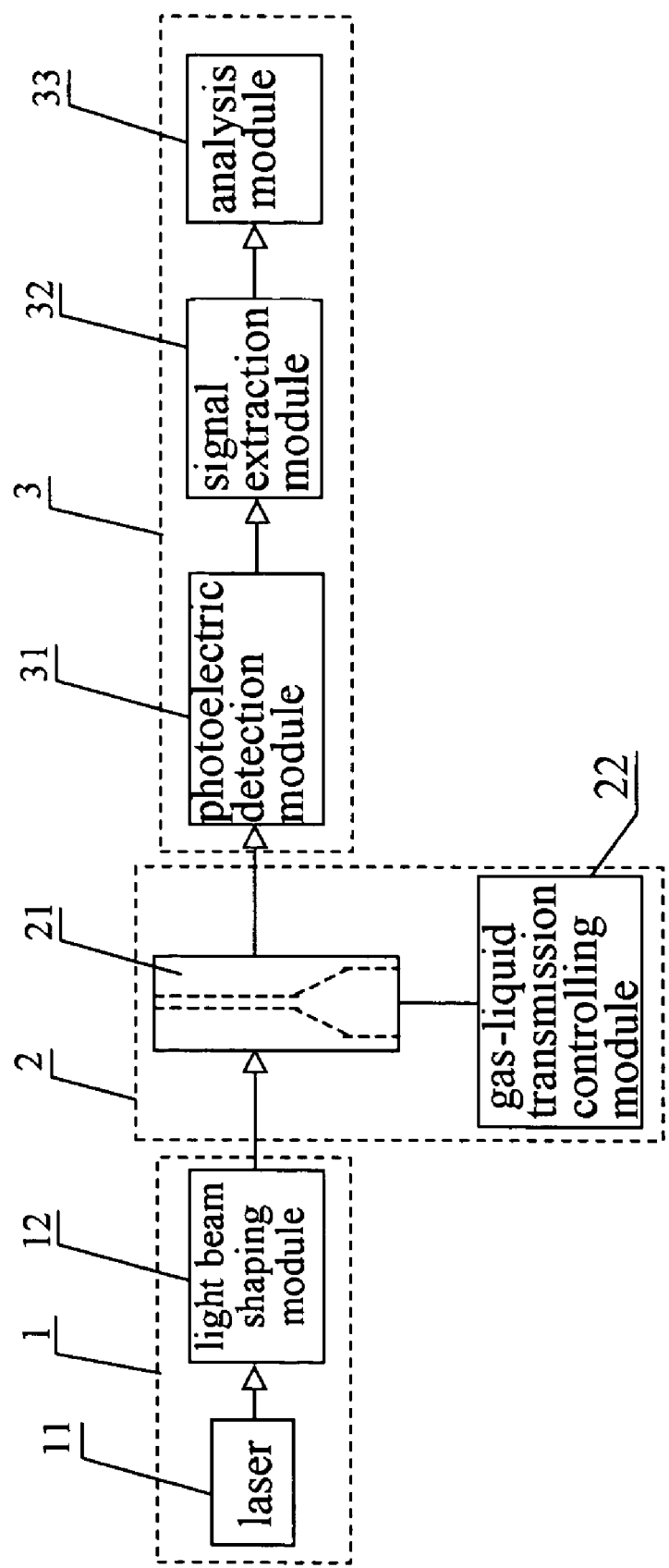
FIG. 4 is a schematic view showing the structure of the system according to the present invention.

The illuminating unit I comprises a laser 11 and a light beam shaping module 12, as shown in FIG. 4.

Figure 6:
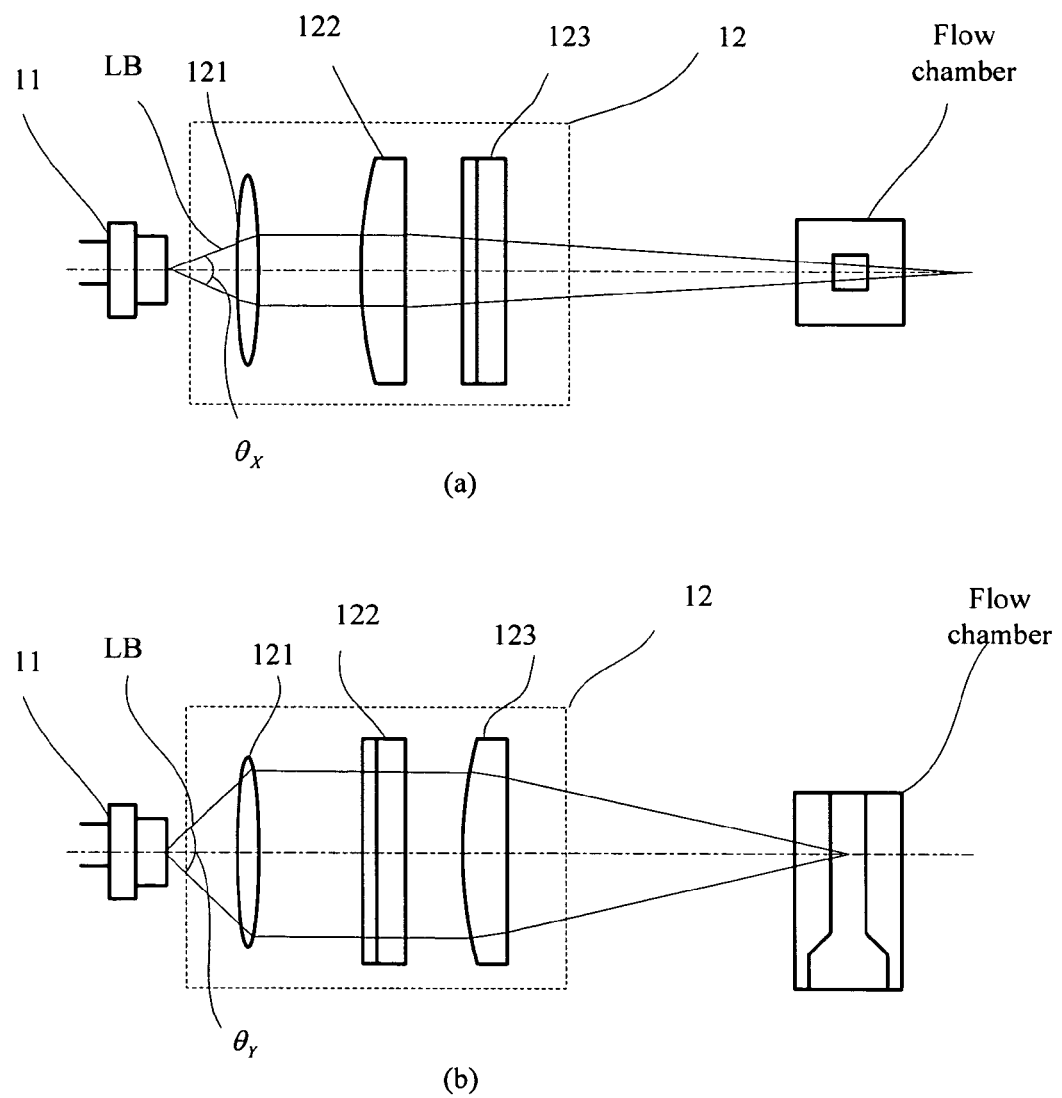
FIG. 6 is a schematic view showing the structure of the light beam shaping module according to the present invention.
Figure 9:
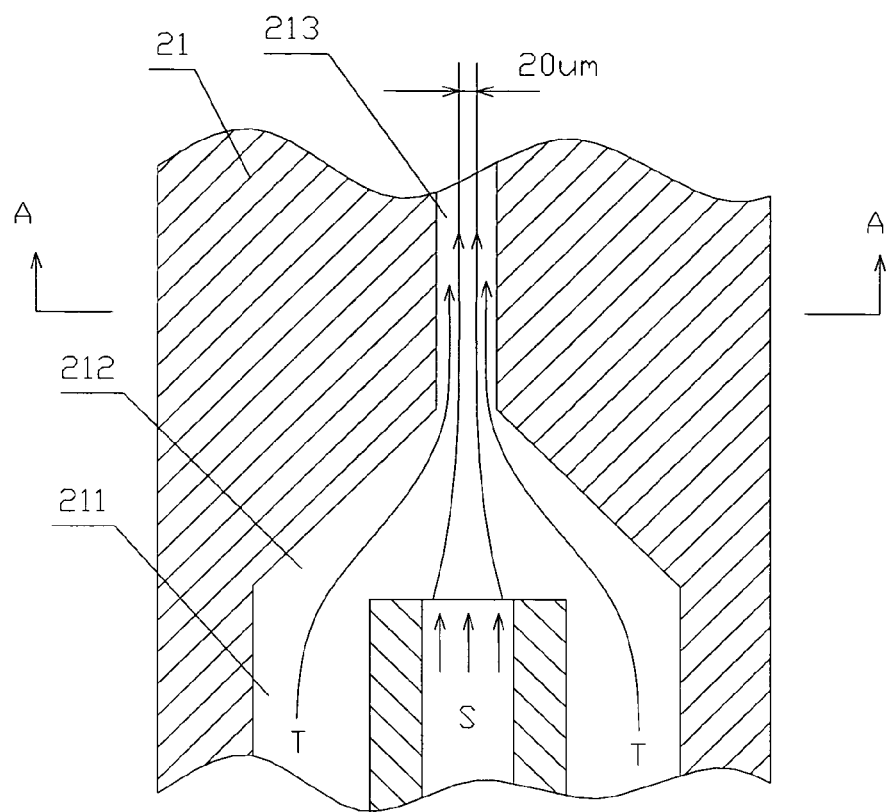
FIG. 9 is a partial view showing the horizontal section of the flow chamber according to the present invention.
Figure 13:
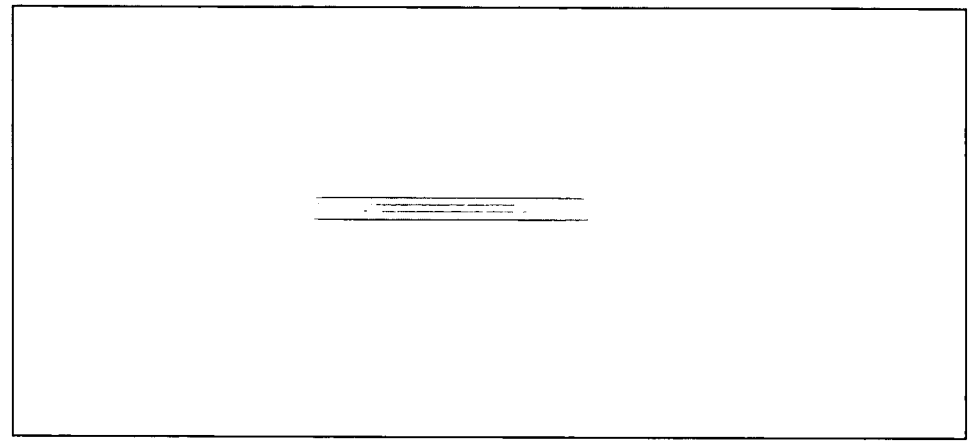
FIG. 13 shows the shape of the section of the irradiating light beam at the flow chamber and the distribution thereof in the direction of the major axis.
Figure 13:
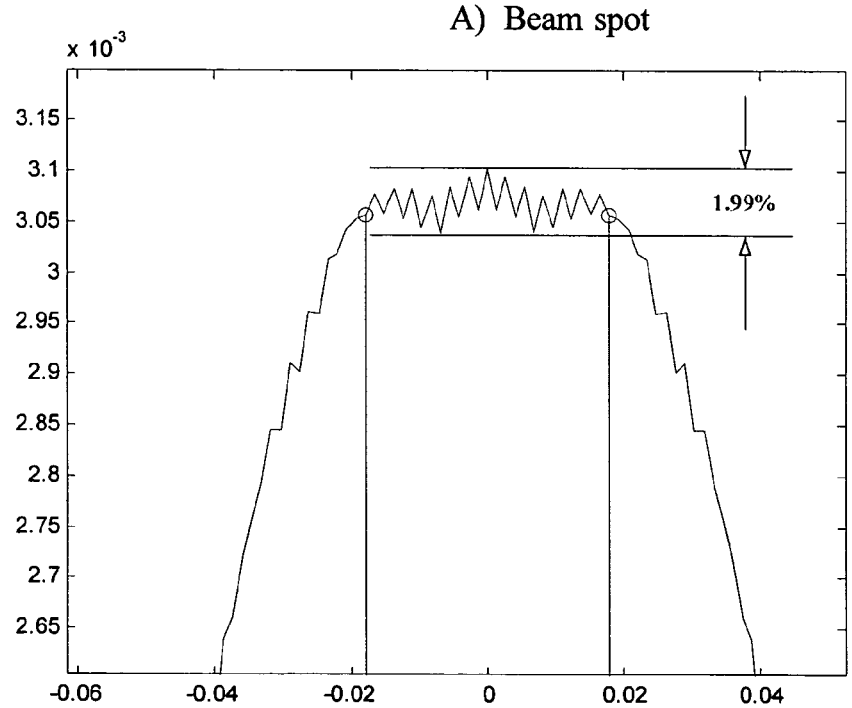

The light beam shaping module 12 is used for collimating and shaping the laser light beam emitted from the laser 11. As shown in FIG. 6, the module 12 comprises a piece of aspheric collimating lens 121 and a pair of mutually crossing cylindrical lens 122 and 123 functional as outputting a light beam with an elliptical cross section which irradiates onto the cells flowing within the flow chamber 21. The length of the minor axis of the ellipse is about 15 µm-25 µm and that of the major axis is about 160 µm-220 µm, and moreover the distribution of the light intensity forms a segment of flat top in the direction of the major axis. The direction of the minor axis coincides with the flowing direction of the liquid (e.g., cells) within the flow chamber 21, and the direction of the major axis is perpendicular to the plane which is defined by the flowing direction of the liquid (e.g., cells) and the transmitting direction of the light beam. The irradiation depth of the light beam is about 8 µm-12 µm. In the present embodiment, the minor axis of the ellipse is preferably 20 µm, the major axis is preferably 200 µm, and the irradiation depth of the light beam is preferably 10 µm, whereby an irradiated region of 20 µm (in the cell flowing direction)×10 µm (in the light beam transmitting direction)×200 µm (in the direction perpendicular to the plane which is defined by the cell flowing direction and the light beam transmitting direction) is formed in the detection zone 213 (i.e., the cell-interrogation zone), as shown in FIG. 9. When cells are passing through this irradiated region, the light that irradiates onto the cells will be scattered. The spot formed by the light beam shaping module and the distribution of light intensity thereof in x direction (i.e., in the direction of the major axis of the spot) is shown in FIG. 13.

Figure 7:
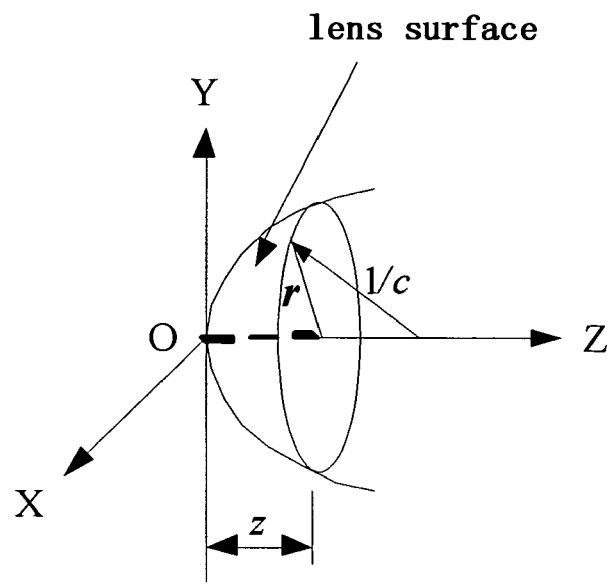
FIG. 7 is a schematic view showing the curved structure of the lens surface of the collimating lens according to the present invention.

In the present embodiment, the numerical aperture of the single collimating lens 121, which takes the form of an aspheric lens, is about 0.3-0.5, and the shape of its lens surface is defined by the following formula:

$$z = \frac{cr^2}{1 + \sqrt{1 - (1+k)c^2 r^2}} + \alpha_1 r^2 + \alpha_2 r^4$$

wherein, as shown in FIG. 7, c is the curvature, z is the axial distance of the cross-section from the fixed point, k is a quadratic constant, and r is the radius of the cross-section.

In addition, the light beam shaping module 12 may only comprise at least one aspheric collimating lens 121 with a numerical aperture no less than 0.3.

Figure 8:
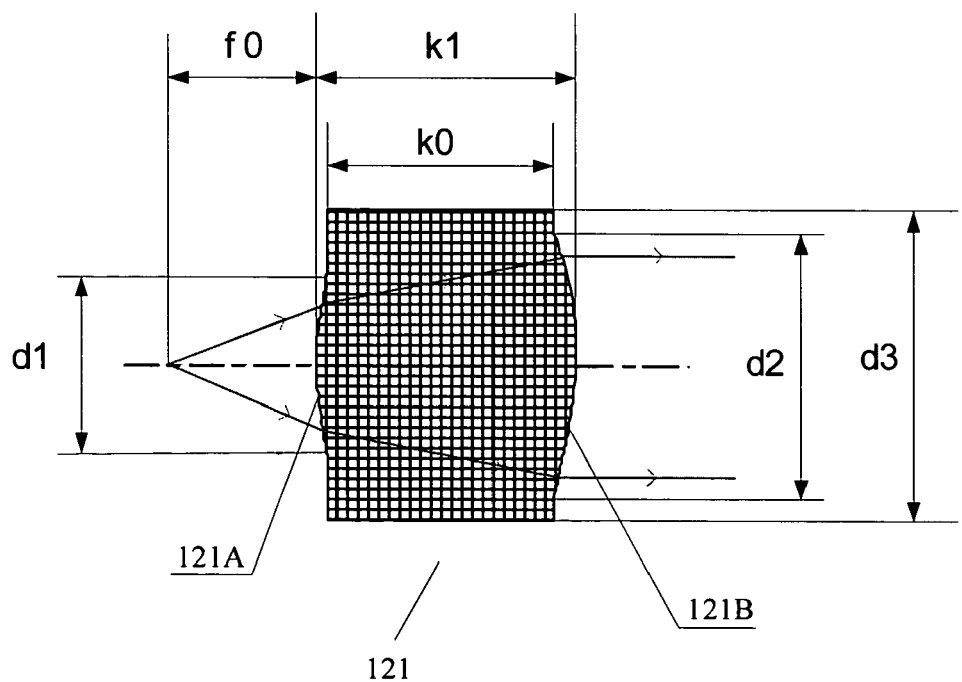
FIG. 8 is a schematic view showing the structure of the collimating lens according to the present invention.

As shown in FIG. 8, the aspheric collimating lens 121 comprises a first lens surface 121A and a second lens surface 121B, wherein the first lens surface is the incidence plane of the laser light beam, and the parameters of the first lens surface 121A and second lens surface 121B are as follows:

| | c | k | α1 | α2 |
|---|---|---|---|---|
| First lens surface | 0.068609 | −87.228063 | 9.15754E−04 | −8.64353E−05 |
| Second lens surface | −0.231481 | −0.648067 | −1.65853E−04 | 8.28138E−06 |

In the present embodiment, as shown in FIG. 8, the clear aperture d1 of the first lens surface 121A is 4.4 mm; the clear aperture d2 of the second lens surface 121B is 5.87 mm; the aperture d3 of the collimating lens 121 is 7.20 mm; the thickness k0 of the collimating lens 121 is 4.21 mm; the center-to-center distance k1 of the collimating lens121 is 5.36 mm; and the center distance f0 between the focal plane and the first lens surface 121A is 3.44 mm.

Thus, in the present embodiment, the collimating lens 121 with a numerical aperture up to 0.4 is used for effectively eliminating the spherical aberration by collimating or focusing the light beam with a 30° aperture angle. Its contribution for the present invention is to eliminate the above mentioned side lobes of the spot so as to reduce the difficulty in the signal pulse recognition.

Figure 5:
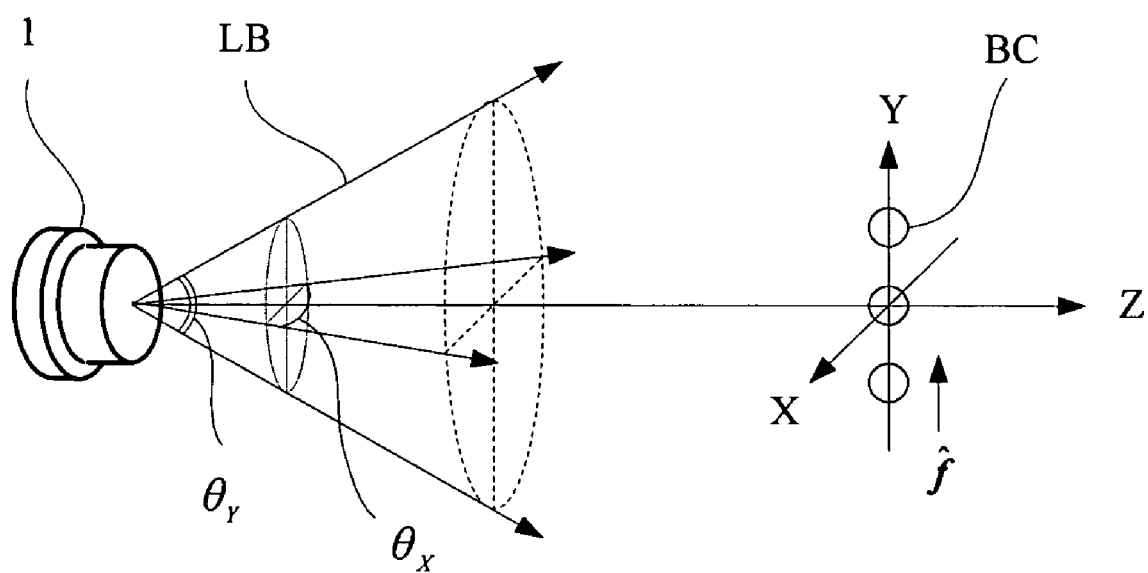
FIG. 5 is a schematic view showing the light beam emitted from the semiconductor laser according to the present invention.

As shown in FIG. 5, the laser 11 in the present embodiment is a semiconductor laser emitting the light beam LB which has different divergence angles in two directions. Assuming that the transmitting direction of the light is along Z axis, the light beam divergence angle θ x in X direction would be different from the divergence angle θ y in Y direction. If θ x<θ y, then the section of the light beam would be an elliptical spot with the major axis in Y direction. At the time of disposing the semiconductor laser, the direction of the smaller divergence angle of the original exit light beam of the semiconductor laser should be kept consistent with the cell flowing direction, so that the spot will have a relatively small size (i.e., minor axis) in the cell flowing direction $\hat{f}$, as shown in FIG. 5. Assuming that the cell flowing direction is in Y direction, then it is necessary that θ x>θ y when disposing the semiconductor laser.

In the present embodiment, the divergence angles of the light beam emitted from the laser 11 in two directions perpendicular to each other are 30° and 18° respectively, with a maximum output power 10 mW, operating power 5 mW and wavelength 670 nm.

Figure 10:
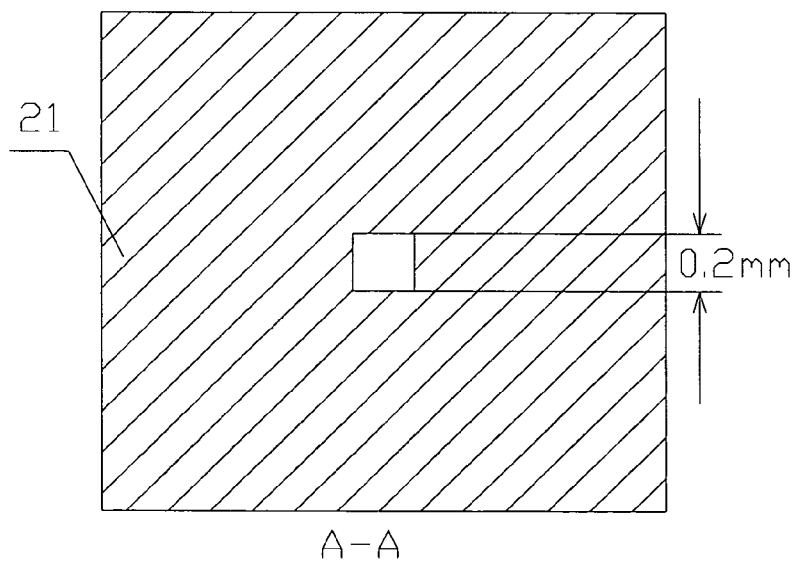
FIG. 10 is a schematic view showing the section of the flow chamber along line A-A according to the present invention.

As shown in FIG. 4, the sample generation unit 2 comprises a gas-liquid transmission control module 22 and a flow chamber 21 which are connected with each other. The gas-liquid transmission control module 22 is used for carrying out the pneumatic transmission of the sample, the sheath fluid, various reagents, cleaning liquids and waste liquids, and at the same time controlling the various conditions of sample reaction, so that the sample liquid containing the cells to be detected may flow through the flow chamber 21 while being encircled by the sheath fluid, as shown in FIG. 9. The flow chamber 21 is made of quartz glass, in the shape of an elongated prism, and the dimension thereof is 4 mm×4 mm×10 mm. A guiding hole with a square cross section is provided in the flow chamber 21, which hole comprises a rectifying segment 211, an accelerating segment 212 and a detecting segment 213. Introduced in from the rectifying segment 211, the sheath fluid forms a laminar current therein, accelerated through the accelerating segment 212, and at the detecting segment 213 passes through the guiding hole while encasing the sample liquid that is injected in via a sample injection needle. As shown in FIG. 10, the side length of the section of the square guiding hole of the detecting segment 213 is about 100 µm-400 µm, and preferably 200 µm in the present embodiment.

The light beam generated by the illuminating unit 1 irradiates onto the detecting segment 213 of the flow chamber 21, and through the light beam shaping module 12, an irradiated region of 20 µm×10 µm×200 µm as the above is formed in the detecting segment 213 by the light beam. Scattering will occur when cells pass through this region. The scattering light beam is then sent to the signal processing unit 3, which receives and correspondingly processes the scattering light beam passing through the flow chamber 21.

As shown in FIG. 4, the signal processing unit 3 comprises a photoelectric detection module 31, a signal extraction module 32 and an analysis module 33 which are connected in series, wherein the photoelectric detection module 31 collects the scattering light in different angle ranges onto the photoelectric converter, so that the optical information out of the scattering light is converted into the corresponding electrical signal which is then sent to the signal extraction module 32.

Figure 11:
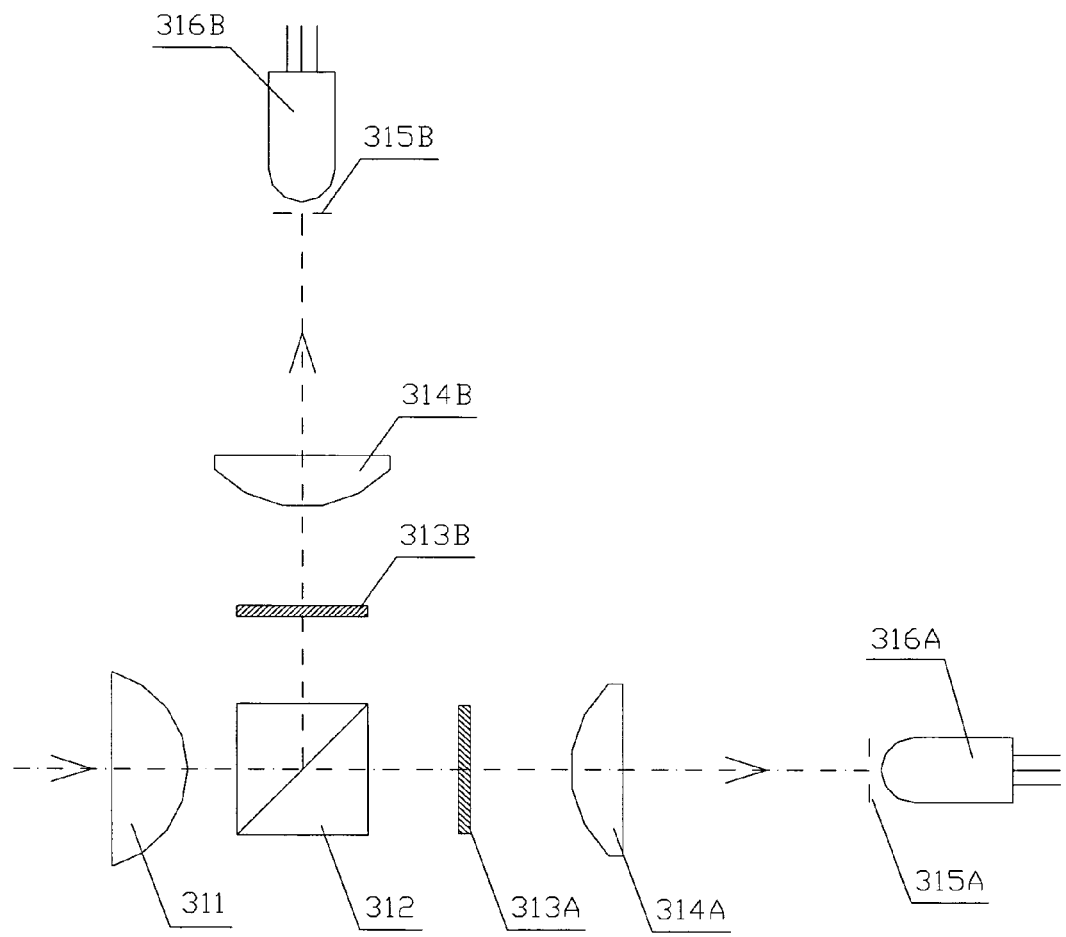
FIG. 11 is a schematic view showing the structure of the photoelectric detection module according to the present invention.

As shown in FIG. 11, at least one piece of aspheric collimating lens may be provided for the photoelectric detection module 31 to collimate the scattering light beam through the flow chamber, which is subsequently sent to the photoelectric converter upon sampling. Optionally, a pair of mutually crossing cylindrical lens may be provided for the light beam shaping module. In the present embodiment, the photoelectric detection module 31 comprises two sets of photoelectric signal collecting sub-modules and corresponding photoelectric converters 316A, 316B. The two sets of photoelectric signal collecting sub-modules respectively collect optical signals with different scattering angles, and the photoelectric converters perform corresponding photoelectric conversion for the optical signals. In particular, the photoelectric detection module 31 comprises a collimating lens 311, a light-splitting prism 312, annular diaphragms 313A, 313B, condensers 314A, 314B, small hole diaphragms 315A, 315B and photoelectric converters 316A, 316B.

As shown in FIG. 11, the photoelectric signal collecting sub-module is accordingly comprised of the annular diaphragms 313A, 313B and the condensers 314A, 314B, wherein the clear apertures of the annular diaphragms 313A and 313B are different, which may be employed respectively to collect the scattering light within different angle ranges.

In the present embodiment, as shown in FIG. 11, the scattering light, after collimated by the collimating lens 311, is divided into two beams by the light-splitting prism 312, and the range of the scattering light collected by the two sets of photoelectric signal collecting sub-module is determined by the focal length of the collimating lens 311 and the clear apertures of the annular diaphragms 313A, 313B.

For example, if the range of the scattering light to be collected is $[\theta_1, \theta_2]$ the clear aperture of the annular diaphragm 313A or 313B will be:

[F*tan $\theta_1$, F*tan $\theta_2$], wherein F is the focal length of the collimating lens 311.

In the present embodiment, the two sets of photoelectric signal collecting sub-modules respectively collect the scattering light in the range of 1~5°, referred to as small angle forward scattering light LAS, and the scattering light in the range of 8~20°, referred to as moderate angle forward scattering light MAS. These two beams of scattering lights are respectively collected by the focusing lens to the photoelectric converters 316A, 316B for photoelectrical conversion and forming electrical signal which is sent to the signal extraction module 32.

Figure 12:
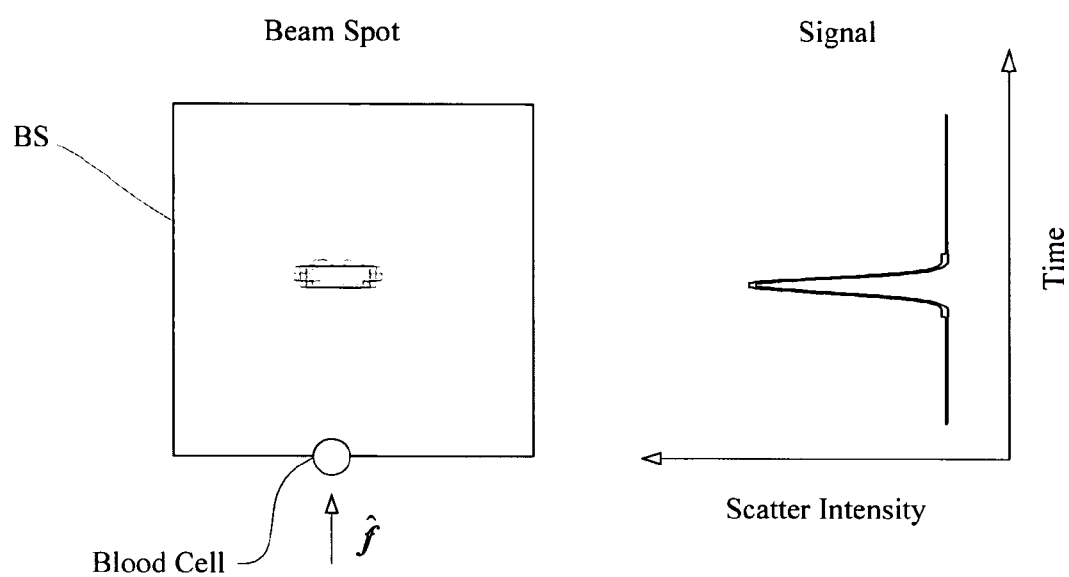
FIG. 12 shows the application of the scattered signal of the present invention.

As shown in FIG. 4, the signal extraction module 32 extracts the peak or pulse width information from the signal so that such information is sent to the analysis module 33. The analysis module 33 uses the received signals for counting and classification to form a one-dimensional histogram or two-dimensional scatter diagram, and then displaying or printing the result of analysis. As shown in FIG. 12, by applying the scattered signal of the present embodiment, the side lobes of the irradiating spot is eliminated, whereby excellent result is achieved.

In the present embodiment, for the collection of such scattering light with a relatively large angle or irradiating spot, the collimating lens 311 may also individually use an aspheric lens surface which is the same as or similar to that of the collimating lens 121, or use such an aspheric lens surface together with the collimating lens 121, the structure of which is the same as or similar to that of the collimating lens 121 and is omitted here.

Although particular embodiments of the present invention have been shown and described, it should be understood that the above discussion is for descriptive purpose and not intended to limit the present invention. Those skilled in the art will appreciate that various modifications, alternatives, variations and equivalents may be made without departing from the scope and spirit of the present invention. Thus, the present invention is intended to cover various modifications, alternatives, variations and equivalents that may fall within the scope and spirit of the present invention as defined by the appended claims.

What is claimed is:

1. A cytometer, comprising:
an illuminating unit comprising a laser and a light beam shaping module for shaping and converging a laser light beam emitted from the laser, so that the light beam irradiates a sample to be detected;
a sample generation unit comprising a gas-liquid transmission controlling module and a flow chamber which are connected to each other, so that a sample liquid containing cells to be detected may flow through the flow chamber while being encircled by a sheath fluid; and
a signal processing unit, comprising at least a photoelectric detection module, for receiving, photoelectrically converting and correspondingly processing scattering light emitted from the flow chamber;
wherein the light beam shaping module comprises at least one aspheric collimating lens with a large numerical aperture and a pair of mutually crossing cylindrical lenses, the pair of mutually crossing cylindrical lenses configured to increase uniformity of the light intensity distribution along a major axis of a cross-section of the light beam.

2. The cytometer of claim 1, wherein the numerical aperture of the aspheric collimating lens is at least 0.3.

3. The cytometer of claim 1, wherein the collimating lens comprises a first lens surface and a second lens surface, the first lens surface being an incidence plane of the laser light beam; and wherein the lens surfaces of the aspheric collimating lens satisfy the following formula:

$$z = \frac{cr^2}{1 + \sqrt{1 - (1+k)c^2r^2}} + \alpha_1 r^2 + \alpha_2 r^4,$$

in which c is a curvature, z is an axial distance of a cross-section from a fixed point, k is a quadratic constant, and r is a radius of the cross-section; and parameters of the first lens surface and the second lens surface are as follows:

|  | c | k | α1 | α2 |
|---|---|---|---|---|
| First lens surface | 0.068609 | −87.228063 | 9.15754E−04 | −8.64353E−05 |
| Second lens surface. | −0.23148106 | −0.648067 | −1.65853E−04 | 8.28138E−08 |

4. The cytometer of claim 1, wherein:
the light beam shaping module outputs a light beam with an elliptical cross section, which irradiates into the flow chamber; the length of a minor axis of the ellipse is 15 μm-25 μm, and that of a major axis is 160 μm-220 μm, wherein the direction of the minor axis coincides with a flowing direction of the liquid within the flow chamber, and a direction of the major axis is perpendicular to a plane which is defined by the flowing direction of the liquid and a transmitting direction of the light beam; and an irradiation depth of the light beam is 8 μm-12 μm, and the light intensity is uniformly distributed at a segment in the direction of the major axis.

5. The cytometer of claim 1, wherein the signal processing unit comprises the photoelectric detection module, a signal extraction module and an analysis module which are connected in series, wherein:
the photoelectric detection module is used for collecting the scattering light in different angle ranges onto a photoelectric converter, so that the optical information out of the scattering light is converted into a corresponding electrical signal which is then sent to the signal extraction module;
the signal extraction module is used for extracting a peak or pulse width information from the signal so that such information is sent to the analysis module; and
the analysis module is used for counting and classifying the received signals to form a one-dimensional histogram or two-dimensional scatter diagram.

6. The cytometer of claim 5, wherein the photoelectric detection module comprises two sets of photoelectric signal collecting sub-modules for respectively collecting optical signals with different scattering angles, and corresponding photoelectric converters for performing corresponding photoelectric conversion for the optical signals.

7. A cytometer, comprising:
an illuminating unit comprising a laser and a light beam shaping module for shaping and converging a laser light beam emitted from the laser, so that the light beam irradiates a sample to be detected;
a sample generation unit comprising a gas-liquid transmission controlling module and a flow chamber which are connected to each other, so that a sample liquid containing cells to be detected may flow through the flow chamber while being encircled by sheath fluid; and
a signal processing unit, at least comprising a photoelectric detection module for receiving, photoelectrically converting and correspondingly processing a scattering light emitted from the flow chamber;
wherein the photoelectric detection module comprises at least one aspheric collimating lens for collimating the scattering light beam emitted from the flow chamber; and wherein the light beam shaping module further comprises a pair of mutually crossing cylindrical lenses, the pair of mutually crossing cylindrical lenses configured to increase uniformity of the light intensity distribution along a major axis of a cross-section of the light beam.

8. The cytometer of claim 7, wherein a numerical aperture of the aspheric collimating lens is at least 0.4.

9. The cytometer of claim 7, wherein the collimating lens comprises a first lens surface and a second lens surface, the first lens surface being an incidence plane of the laser light beam; and wherein the lens surfaces of the collimating lens satisfy the following formula:

$$z = \frac{cr^2}{1+\sqrt{1-(1+k)c^2r^2}} + \alpha_1 r^2 + \alpha_2 r^4 + \alpha_3 r^6,$$

in which c is a curvature, z is an axial distance of a cross-section from a fixed point, k is a quadratic constant, and r is a radius of the cross-section.

10. The cytometer of claim 7, wherein the light beam shaping module outputs a light beam with an elliptical cross section, which irradiates into the flow chamber; the length of a minor axis of the ellipse is 15 μm-25 μm, and that of a major axis is 160 μm-220 μm, wherein a direction of the minor axis coincides with a flowing direction of the liquid within the flow chamber, and the direction of the major axis is perpendicular to a plane which is defined by the flowing direction of the liquid and a transmitting direction of the light beam; and an irradiation depth of the light beam is 8 μm-12 μm.

11. The cytometer of claim 7, wherein the signal processing unit comprises the photoelectric detection module, a signal extraction module and an analysis module which are connected in series, wherein:
the photoelectric detection module is used for collecting the scattering light in different angle ranges onto a photoelectric converter, so that the optical information out of the scattering light is converted into a corresponding electrical signal which is then sent to the signal extraction module;
the signal extraction module is used for extracting peak or pulse width information from the signal so that such information is sent to the analysis module; and
the analysis module is used for counting and classifying the received signals to form a one-dimensional histogram or two-dimensional scatter diagram.

12. The cytometer of claim 11, wherein the photoelectric detection module comprises two sets of photoelectric signal collecting sub-modules for respectively collecting optical signals with different scattering angles, and corresponding photoelectric converters for performing corresponding photoelectric conversion for the optical signals.

13. The cytometer of claim 7, wherein the laser is a semiconductor laser.

* * * * *